United States Patent [19]

Stemple

[11] Patent Number: 4,566,457

[45] Date of Patent: Jan. 28, 1986

[54] DEFIBRILLATOR CIRCUIT AND ELECTRODES THEREFOR

[76] Inventor: Gunter Stemple, Thorstrasse 13, D-8912 Kaufering, Fed. Rep. of Germany

[21] Appl. No.: 757,775

[22] Filed: Jul. 24, 1985

Related U.S. Application Data

[63] Continuation of Ser. No. 519,843, Aug. 3, 1983, abandoned.

[30] Foreign Application Priority Data

Aug. 4, 1982 [DE] Fed. Rep. of Germany ....... 3229134

[51] Int. Cl.[4] ............................................. A61N 1/36
[52] U.S. Cl. ................................ 128/419 D; 128/783
[58] Field of Search .................... 128/419 D, 783, 802

[56] References Cited

U.S. PATENT DOCUMENTS

| | | | |
|---|---|---|---|
| 2,978,084 | 4/1961 | Vilkaitis | 128/802 |
| 3,224,447 | 12/1965 | Becker et al. | 128/419 D |
| 3,389,703 | 6/1968 | Criswell et al. | 128/419 D |
| 3,543,761 | 12/1970 | Bradley | 128/419 E |
| 3,747,605 | 7/1973 | Cook | 128/419 D |
| 3,862,636 | 1/1975 | Bell et al. | 128/419 D |
| 4,440,172 | 4/1984 | Langer | 128/419 D |

*Primary Examiner*—William E. Kamm
*Attorney, Agent, or Firm*—Stevens, Davis, Miller & Mosher

[57] ABSTRACT

Defibrillator electrode and electrical circuit for generating pulses of energy at the electrodes of a defibrillator comprises an energy storage means, and a switch for supplying energy to the electrodes from the storage means, when the switch is closed. A shunt switch is connected in parallel with the energy storage means, and to a junction on the output side of the supply switch, to form a safety circuit. The shunt switch has a normally closed condition in which it shunts the electrodes, being opened only for the duration of the shock treatment.

24 Claims, 11 Drawing Figures

DEFIBRILLATOR CIRCUIT AND ELECTRODES THEREFOR

This application is a continuation of application Ser. No. 519,843, filed Aug. 3, 1983, now abandoned.

BACKGROUND OF THE INVENTION

The invention relates generally to defibrillator electrodes and more specifically to an electrical circuit for generating pulses of energy at two stock electrodes of such a defibrillator.

A known form of defibrillator comprises an energy storage means such as a capacitor, and an operating switch which is closed in order for the energy stored in the capacitor to be supplied in pulse form to the shock electrodes of the defibrillator, when a patient is to be subjected to shock treatment thereby. The energy storage means can store energy in stepped or graduated quantities, and correspondingly graduated quantities of energy can be delivered, in dependance on the patient and the desired type of treatment. The amounts of energy delivered for external defibrillation may be between for example 20 and 320 Joules. Hitherto, from the point of view of patient safety, it was generally considered sufficient for the transfer of energy between the energy storage means or capacitor and the defibrillator electrodes to take place by way of an operating or working switch which is closed only for the duration of the defibrillation procedure. In other words, in that defibrillator design, the patient being treated is connected into the working circuit which comprises the capacitor and the operating switch. However, such an arrangement may involve a certain risk in regard to patient safety, particularly if there is a defect in the energy storage means or the switch.

SUMMARY OF THE INVENTION

An object of the present invention is to provide an improved electrical circuit for generating energy pulses at the shock electrodes of a defibrillator.

Another object of the present invention is to provide an electrical circuit for energy pulse generation at the electrodes of a defibrillator, wherein a patient to be treated is galvanically separated from the operating circuit of the arrangement.

Yet another object of the present invention is to provide an electrical circuit for generating energy pulses at two shock electrodes of a defibrillator, wherein components which are provided for safety discharge of the circuit and for removal of the energy stored in an energy storage means of the circuit no longer have to be constantly monitored.

A further object of the invention is to provide an electrical circuit for generating energy pulses at two defibrillator shock electrodes, including means for carrying unrequired energy away by means of internal discharging.

A still further object of the invention is to provide such an electrical circuit for a defibrillator, wherein internal discharging to remove unrequired energy occurs rapidly after a shock procedure.

These and other objects are achieved by means of an electrical circuit for generating pulses of energy at two shock electrodes of a defibrillator, having an energy storage means such as a capacitor, the energy stored in which is discharged in a pulse manner to the shock electrodes by way of a closed operating switch, when a patient is to be subjected to a shock treatment. A shunt contact means is connected in parallel with the energy storage means and to a branch junction on the output side of the operating switch. The shunt contact means which has a normally closed condition shunts the two shock electrodes thereby, and is opened only for the duration of the defibrillation or shock procedure.

With an arrangement as set forth above in accordance with the principles of this invention, the patient is separated from the operating circuit of the defibrillator and the components which are included in the operating circuit such as the energy storage means or capacitor, the operating switch and possibly a discharging resistor, which is disposed in parallel with the energy storage means, and a discharging switch connected in series with that resistor, which serve for safety discharge and by means of which the energy stored in the energy storage means can be safely dissipated, no longer have to be monitored with the same amount of care and attention in order to safeguard patient safety. The above-mentioned series circuit comprising the discharging switch and resistor serve to carry away energy that is not required, by internal discharging. That is also important in the case of a power failure because in that case a means such as a relay for actuating the shunt contact means is released and closes the shunt contact means. In addition, internal discharge takes place for example after about 10 ms duration of the defibrillation or shock procedure.

It will be appreciated that the shunt contact means which forms a safety circuit is only opened when there is a specific intention to apply a shock procedure, for the duration of that procedure. The shunt contact means remains closed if there is no intention of triggering off a defibrillation shock procedure. If for any reason a mistake is made and for example the operating switch is accidentally operated, the energy will not be transmitted into the patient circuit which includes the defibrillation electrodes, but is short-circuited at the shunt contact means.

An inductance which is disposed between the junction point at which the shunt contact means is connected into the circuit, and the operating switch, and which generally serves for shock pulse formation, acts as a current limiting means by virtue of its reactance and effective resistance so that there is no possibility of uncontrolledly high circuit currents flowing through the shunt contact means. That design configuration therefore also protects the operating switch.

In the event that, nonetheless, in the case of an error or defect, a voltage is applied to the closed shunt contact means in the short circuit mode, a respective voltage barrier means, for example in the form of a cold cathode switching tube or valve, may be interposed between the two terminals of the shunt contact means and the two defibrillation electrodes. The voltage barrier means have high firing voltages, for example 180 V for each cold cathode tube.

The cold cathode tubes also serve as a coupling means between the operating and safety circuit and the patient circuit. As the cold cathode tubes, when in the not-fired condition, provide for complete galvanic separation between the operating circuit and the patient circuit, an EKG apparatus may easily be connected to the defibrillation electrodes. The operating circuit and the short circuit in the safety circuit, which occurs by virtue of the shunt contact means being in a closed conditiion, have no influence on the imput impedance of the EKG amplifier.

The circuit is operated by the energy storage means or capacitor first being charged up to a preselected level. The safety circuit is latched in the starting condition by closure of the shunt contact means. In that condition of the arrangement, no energy can flow from the energy storage means into the patient circuit. When a shock is to be triggered off and transmitted to the patient, the safety circuit is released just beforehand by opening the shunt contact means and the energy goes to the electrodes and thus into the patient circuit, by way of the operating switch which is then in a closed condition.

Further objects, features and advantages of the present invention will be more clearly apparent from the following description of the defibrillator circuit in accordance with the principles of the invention.

BRIEF DESCRIPTION OF THE DRAWINGS

FIGS. 8 through 11 show embodiments of defibrillator electrodes.

DESCRIPTION OF THE PREFERRED EMBODIMENT

Reference will now be made to the accompanying drawings to provide a more complete description of an improved electrical circuit for generating pulses at the shock electrodes of a defibrillator for shock treatment of a patient.

Figure 1:
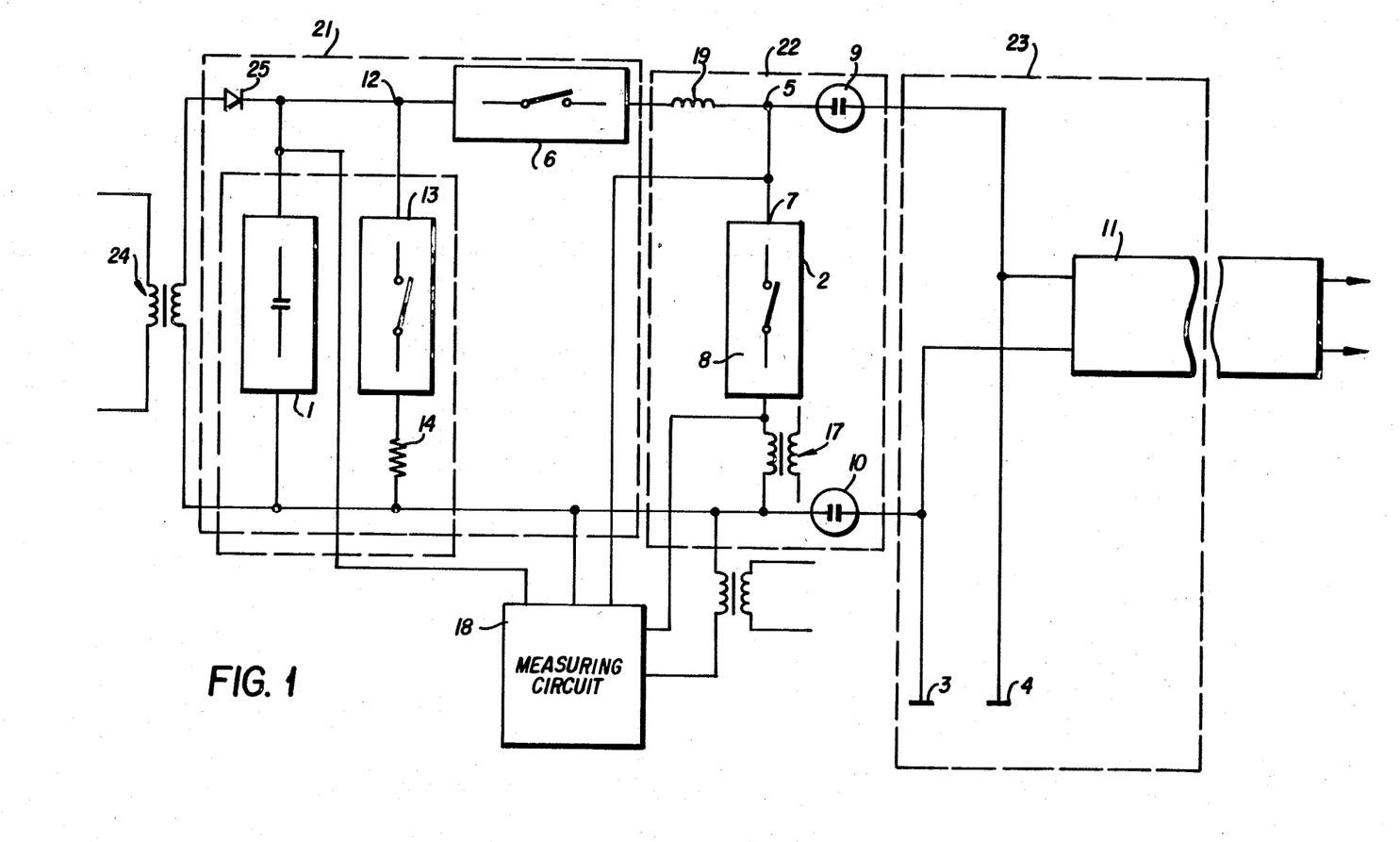
FIG. 1 a block circuit diagram of a defibrillator circuit for generating energy pulses for shock treatment of patients.
Figure 3:
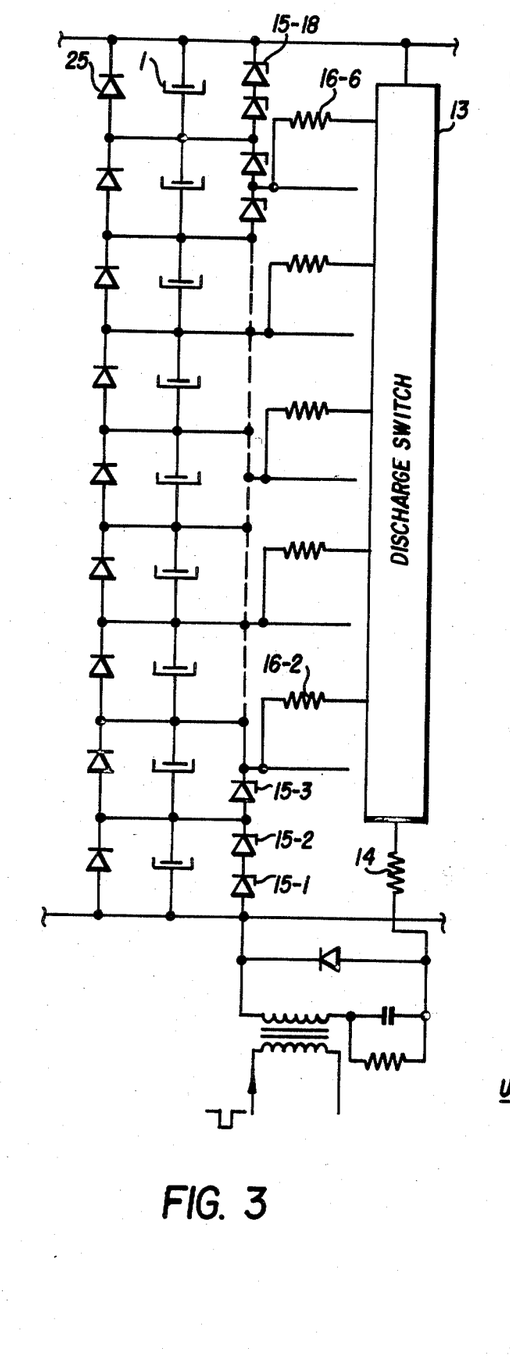
FIG. 3 shows a circuit diagram of the discharging curcuit which is included in the operating circuit.
Figure 4:
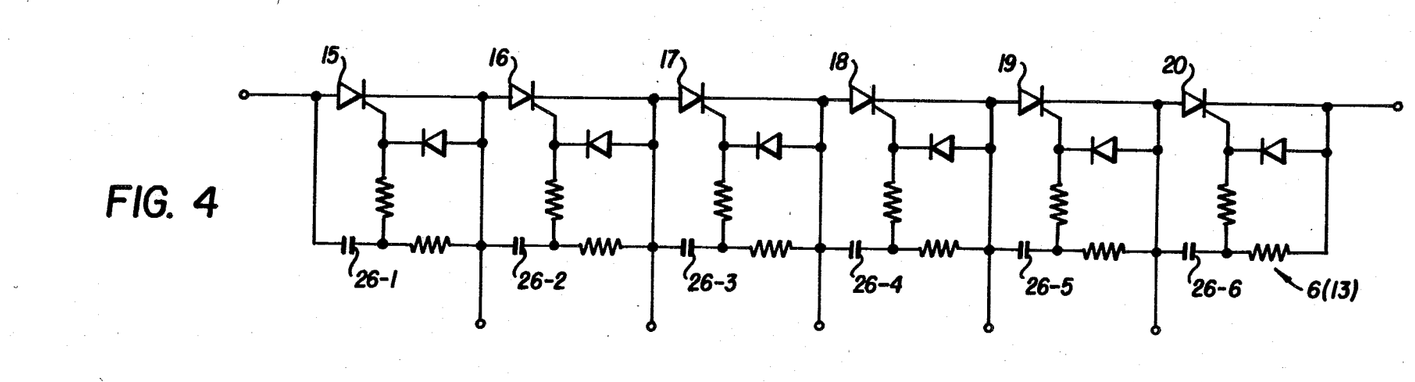
FIG. 4 shows a circuit diagram for the operating switch or discharging switch in the operating circuit.

Referring therefore firstly to FIG. 1, the embodiment shown therein of an electrical circuit for generating energy pulses for an electrical defibrillator for the shock treatment of a patient comprises working or operating circuit 21, a safety circuit 22 and a patient circuit 23. The operating circuit 21 includes an energy storage means 1 in the form of a capacitor or a capacitor cascade arrangement (as shown for example in FIG. 3). the energy storage means 1 is charged up by a transformer charging circuit 24, by way of a suitable rectifier 25, as for example a rectifier cascade array, as shown in FIG. 3. The circuit 21 also includes a working or operating switch 6 which is operatively disposed between one terminal of the energy storage means 1 and a shock electrode 4. As shown in FIG. 4, for example, the switch 1 may comprise a train of thyristors 15 through 20. In addition, in parallel with the energy storage means 1, the operating circuit 21 includes a series circuit comprising a discharging switch 13 and a discharging resistor 14, wherein the switch 13 may be of the same construction as the switch shown in FIG. 4. As shown in FIG. 3, voltage division may be effected by way of the individual capacitors of the capacitor cascade array forming the energy storage means 1, and Zener diodes 15-1 through 15-8 which, by way of resistors 16-2 through 16-6, fix the thyristor potentials.

The above-mentioned safety circuit includes a shunt switch or contact means 2 which is coupled to the patient circuit 23 that is formed by the shock or defibrillation electrodes 3 and 4, by way of voltage barrier means which, in the illustrated embodiment, are formed by cold cathode switching tubes 9 and 10. The shunt contact means 2 is connected in parallel with the energy storage means 1 and has a tapping or branch-off point 5, on the output side of the operating switch 6.

The shunt contact means 2 is normally in a closed condition, that is to say, in a latched or locked condition, so that, if the switch 6 is unintentionally closed, the energy stored in the energy storage means cannot be discharged by way of the electrodes 3 and 4, but only by way of the shunt contact means 2. For limiting the current flow in that situation, the safety circuit may include an inductor 19, for example an air coil, which serves for pulse shaping during the defibrillation shock procedure. As will be clearly seen in FIG. 1, the inductor 19 is connected between the output terminal of the switch 6 and the junction 5.

As the cold cathode switching tubes 9 and 10 provide for complete galvanic separation as between the operating circuit 21 and the patient circuit 23, the circuit 21 has no influence whatever on the imput impedance, connected to the electrodes 3 and 4, of an EKG amplifier of an EKG apparatus as indicated at 11.

Before a defibrillation shock procedure is initiated, a measurement value is taken from the energy storage means 1 and applied to a measuring circuit as indicated at 18 in FIG. 1. The circuit 18 is also supplied with a monitoring voltage $U_U$ (see FIG. 2) which occurs as a high-frequency voltage drop at an inductor 17 connected in series with the shunt contact means 2 (see FIG. 1). The shunt contact means 2 is opened only when the measuring circuit has ascertained that the measurement value and the monitoring voltage are of the required values.

Figure 2:
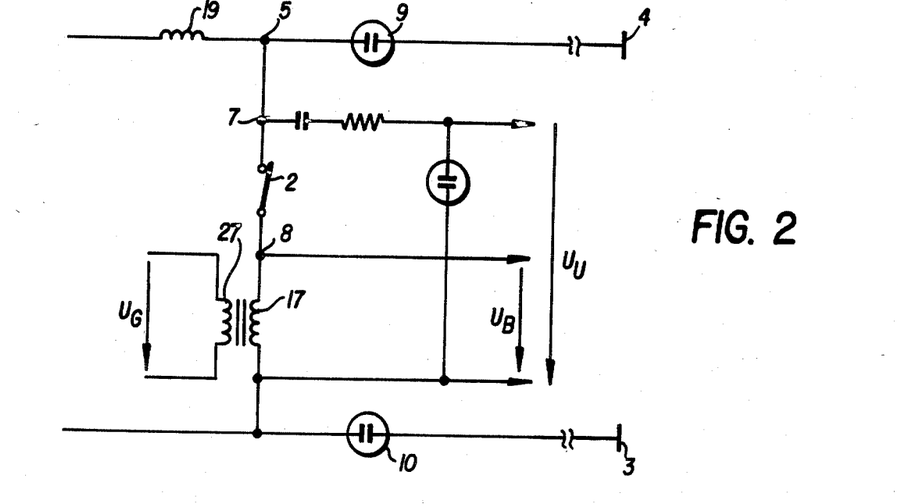
FIG. 2 shows a circuit diagram of the safety circuit and for producing the monitoring voltage at the shunt contact means and the operating voltage for a measuring circuit.

Referring now more particularly also to FIG. 2, the high frequency voltage drop at the inductor 17 is generated by a generator voltage $U_G$, the voltage is tapped off at the inductor 17 supplying the operating voltage $U_B$ for the measuring circuit 18. If the shunt contact means 2 or the shunt circuit which also includes the transformer which is indicated at 27 in FIG. 2 and the effect of which is increased by a capacitance means 26-1 through 26-6 (see FIG. 4) connected between the anode and the control electrode of each thyristor 15 through 20 is unintentionally opened, that fact is noted in the measuring circuit 18, and there is then no possiblilty of a switch-on signal being produced for switching on the switch 6. That arrangement additionally provides monitoring of the shunt contact means 2 forming part of the safety circuit 22. The reason for that is more particularly that in that case the monitoring voltage $U_{\ddot{U}}$ deviates from a perdetermined reference value (logic level).

The switch 6 which is preferably formed by the operating train of thyristors 15 through 20 as shown in FIG. 4 is switched on by a brief pulse applied to the control electrodes of the thyristors. That pulse has a steep du/dt configuration and simultaneously fires the thyristors.

For the purposes of internal discharge of the energy stored in the energy storage means, the above-mentioned discharging switch 13 may be of the same design and configuration as the switch 6, for example, the circuit configuration shown in FIG. 4. In this case also the discharging thyristor array may be fired simultaneously by a pulse having a steep du/dt characteristic.

Figure 5:
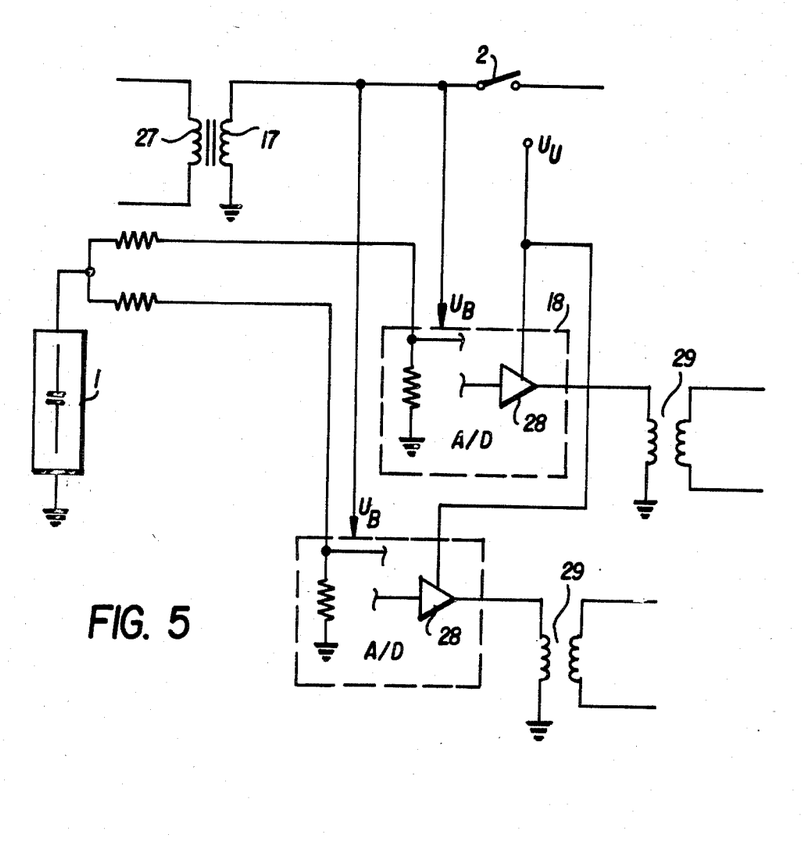
FIG. 5 shows a block circuit diagram of the measureing circuit.

The measurement value which is tapped off from the energy storage means, as referred to hereinbefore, is compared to the reference measurement value and, if the result of the comparison operation is acceptable, the apparatus is ready for the defibrillation shock procedure, on the condition that the monitoring voltage which forms the supply voltage for a driver stage 28 (see FIG. 5) in the measuring circuit 18 is present. Referring still to FIG. 5, the combined measurement value/monitoring signal which is taken out by way of a transformer 29 serves to initiate the defibrillation shock procedure. The defibrillation shock procedure comprises opening of the shunt contact means 2, delayed closure (about 2 ms) of the operating switch 6, and delayed discharge (about 10 ms) through the discharging resistor 14.

Figure 6:
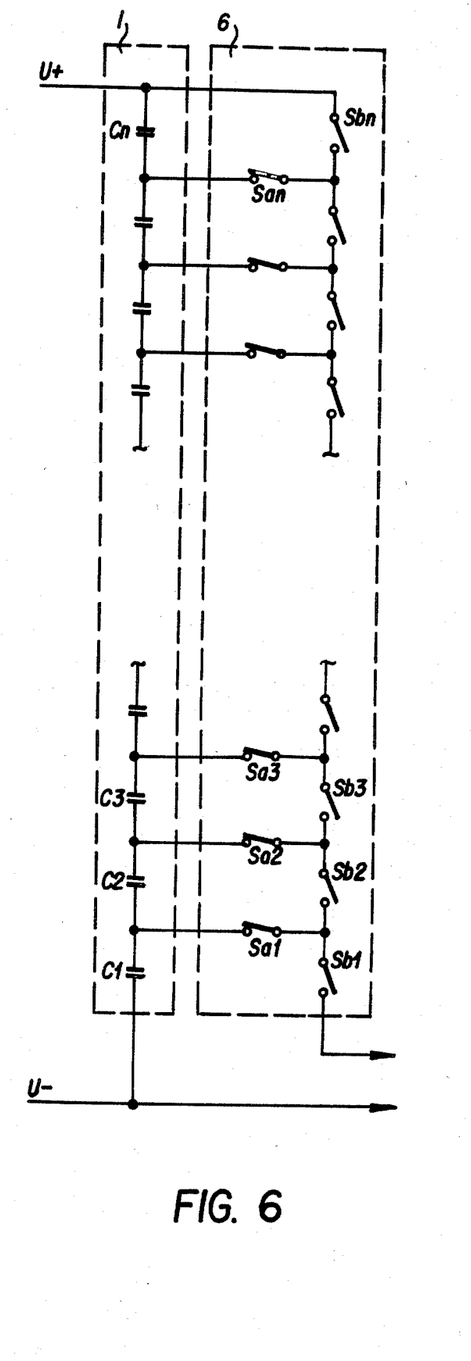
FIGS. 6 and 7 shows embodiments of the energy storage means used in the defibrillator.

Reference will now be made to FIG. 6 which shows an embodiment of the energy storage means and the operating switch 6. As illustrated therein, the energy storage means comprises a plurality of series-connected capacitors $C_1$ through $C_n$. The switch 6 comprises a plurality of switches $Sb_1$ through $Sb_n$ which are also connected in series. The junctions between each two capacitors $C_1$ and $C_2$ through $C_{n-1}$ and $C_n$ are connected to the junctions between two switches $Sb_1$ $Sb_2$ through $Sb_{n-1}$ and $Sb_n$, by way of further switches $Sa_1$ through $Sa_n$. The resulting array and interconnection of capacitors and various switches can be clearly seen from FIG. 6.

The series-connected capacitors $C_1$ through $C_n$ are all charged up to the same voltage level. The capacitors are discharged in a serial mode at precisely determined intervals of time. For that purpose, the switches $Sb_1$ through $Sb_n$ are closed serially at the above-mentioned fixed intervals of time. The respective switch $Sa_1$ through $Sa_n$, by way of which the preceding discharge of a respective capacitor took place, is thereby opened. At the beginning of the discharge procedure, the capacitor $C_1$ is initially discharged, by way of the switch $Sa_1$ which is in a closed condition and the switch $Sb_1$ which is also closed. The switches $Sb_2$ through $Sb_n$ are in an open condition. In order for the capacitor $C_2$ to be discharged, the switch $Sb_2$ is closed and the switch $Sa_1$ is opened. The switch $Sb_1$ remains closed, while the switch $Sa_2$ is also closed. In other words, discharging of the capacitor $C_2$ is by way of the switches $Sa_a$, $Sb_2$ and $Sb_1$. The other capacitors $C_3$ through $C_n$ are also discharged in the same manner. Before the operation of discharging the capacitors begins the switches $Sb_1$ through $Sb_n$ are opened. The switches $Sa_1$ through $Sa_n$ can be closed.

By virtue of the above-described serial mode of building up the individual capacitor voltages, with simultaneous discharge at the shock electrodes, it is possible to produce an individually definable discharge curve.

The switches $Sa_1$ through $Sa_n$ and $Sb_1$ through $Sb_n$ may be for example in the form of diodes, transistors, thyristors and the like.

Figure 7:
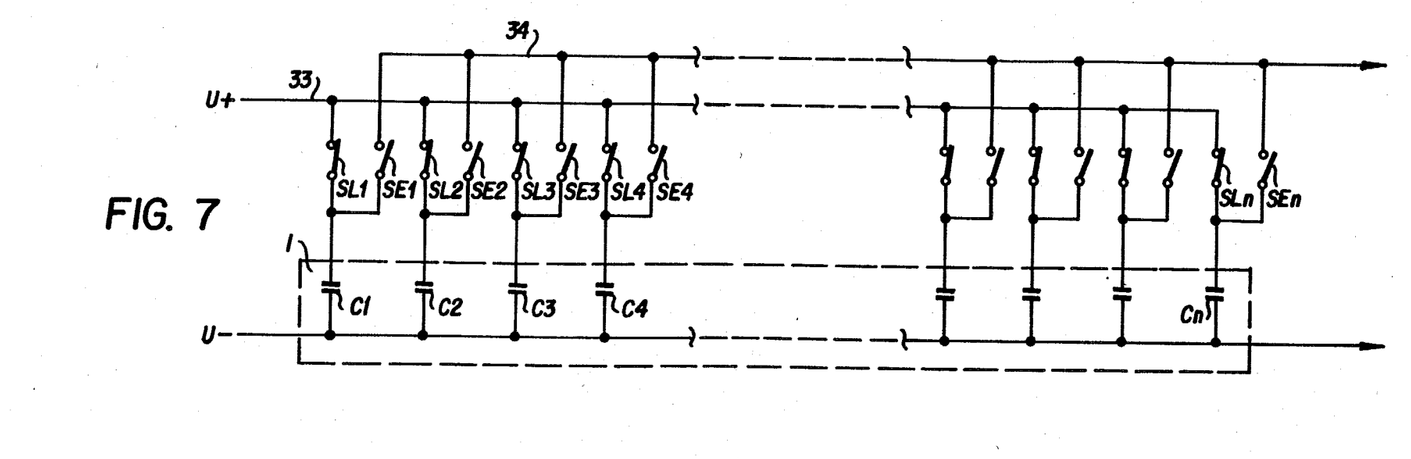

Reference is now made to FIG. 7 showing another embodiment of the energy storage means 1. In the FIG. 7 embodiment, the energy storage means comprises a plurality of capacitors $C_1$ through $C_n$ which are connected in parallel. The illustrated circuit includes a charging line 33 which is connected to the respective capacitors $C_1$ through $C_n$ by way of respective switches $SL_1$ through $SL_n$ which are connected in series with the respective capacitors. The illustrated circuit further includes a discharging line 34 which is also connected to the capacitors $C_1$ through $C_n$ by way of respective switches $SE_1$ through $SE_n$ connected in series with respective ones of the capacitors. It will be seen therefore that discharge of the capacitor array is effected by way of the discharge line 34 when the switches $SL_1$ through $SL_n$ are in an open condition and the switches $SE_1$ through $SE_n$ connected in series with the capacitors are serially closed at given intervals of time. In this case also, the serial combination of the individual capacitor voltages, with simultaneous discharge by way of the electrodes 3 and 4, provides for the formation of an individually definable discharge curve. In the embodiment illstrated in FIG. 7, it will be appreciated that the switches $SE_1$ through $SE_n$ perform the function of the operating switch 6 illustrated for example in the FIG. 1 circuit. The switches $SL_1$ throught $SL_n$ and $SE_1$ through $SE_n$ may also be in the form of diodes, transistors, thyristors and the like suitable means.

Figure 8:
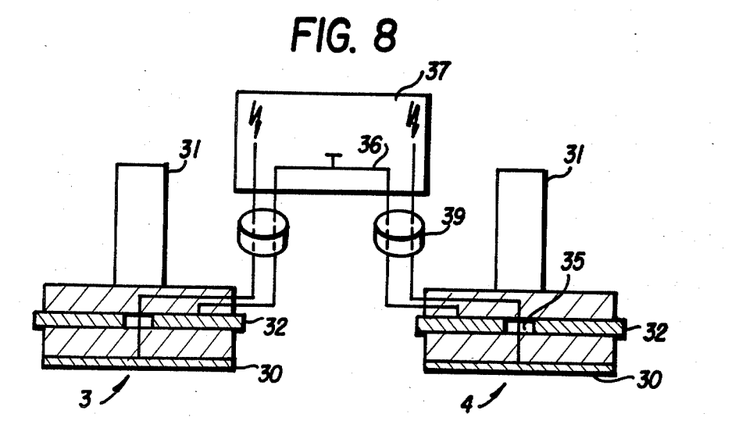
Figure 9:
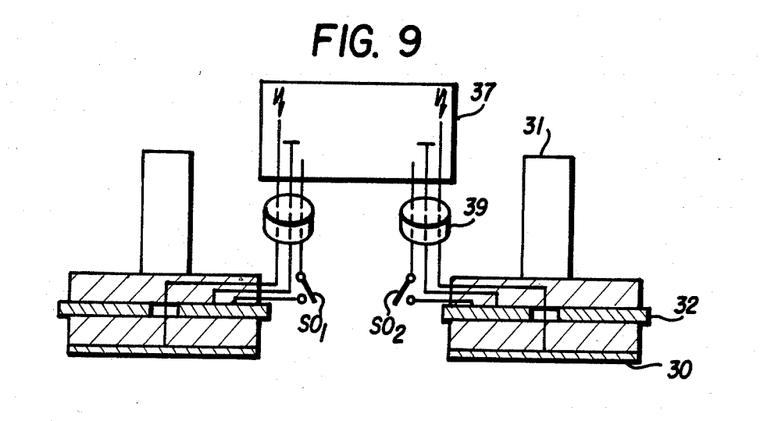
Figure 10:
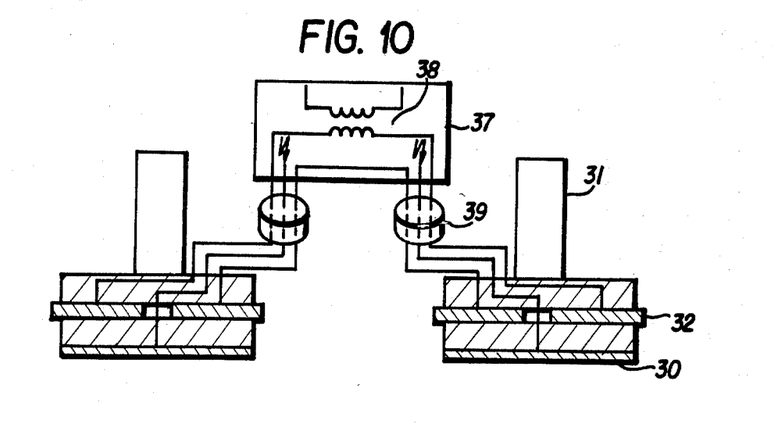

Reference will now be made to FIGS. 8 through 10 showing various embodiments and forms of the shock electrodes 3 and 4.

As shown in FIGS. 8 through 10, each of the shock electrodes 3 and 4 has a handle or gripping member 31, and an applicator electrode member 30 by way of which the energy from the energy storage means 1 is discharged, in the defibrillation procedure. Disposed between the actuating handle 31 and the electrode member 30 in each shock electrode 3 and 4 is a protective electrode 32 which may be of a disc-like or annular configuration and which has at least one surface extending around the outer peripheral surface of the defibrillation electrode. In the embodiments illustrated in FIGS. 8 through 10, the protective electrode 32 projects beyond the outer peripheral surface of the respective electrode 3, 4, by means of a peripheral edge or rim portion.

Each electrode 32 has an aperture or through-feed means which is at 35 disposed for example at a substantially central location, through which passes the power supply line for the electrode member 30 of the respective electrode 3 or 4. As will be clearly seen from FIGS. 8 through 10, the protective electrodes 32 of the two defibrillator electrodes 3 and 4 are connected together by way of a line 36. The line 36 may go by way of the defibrillator apparatus 37. In order to provide for monitoring of the electrically conducting connection between the two protective electrode member 32, the connection may be made for example by way of a control line. For that purpose, as shown in FIG. 9, the arrangement may include additional switches as indicated at SO1 and SO2. In the construction illustrated in FIG. 10, the connection between the two protective electrode members 32 is monitored by way of a coupler 38 and two wires.

The specific configuration of the defibrillator electrodes with protective electrode members 32 is provided to avoid the danger of electric shocks for the defibrillator operator, which may be caused by virtue of conducting surface fouling on the defibrillator electrodes. Defibrillator equipment should be easy to transport, and an open mode of construction or design is therefore preferred. With that kind of design configuration, the defibrillator electrodes are not protected against wetness and fouling or soiling from the exterior. In addition, a conducting gel which is painted on the electrode surface is frequently used for making good contact between the patient's skin and the applicator electrode members. That application of gel also increases the risk of electrical leakage paths being formed between the applicator electrode member 30 and the operator handle 31. In order not to provide absolute protection for the operator, from such leakage currents, the protective electrode is disposed between the handle 31 and the applicator electrode member 30.

As will be clearly seen from FIGS. 8 through 10, the lines for the electrode member 30 and the protective electrode 32 may be disposed in common cables 39.

FIG. 11 shows a paddle- or spoon-shaped electrode which can be placed directly against a heart muscle. This electrode has an application electrode 30' in the shape of the spoon or paddle and is placed against the heart muscle for internal use in the case of defibrillation. In the stem-shaped operating handle 31' there is provided a circumferential protective electrode 32' which has a supply line lead-through 35'. In a common cable 39' both the supply line for the application electrode 30' and the line connected to the protective electrode 32' are carried away by the stem-shaped operating handle 31'. These wires can be interconnected in the same manner as shown in the embodiments of FIGS. 8-10.

It will be appreciated therefore that the above-described constructions of the electrical circuit for a defibrillator provide for the generation of energy pulses at the electrodes of the defibrillator, wherein the patient is safeguarded and separated from the operating circuit of the defibrillator apparatus. In addition, with the described construction, there is no longer any need for constant monitoring or checking of components of the arrangement which are provided for safety discharge of the circuit and by way of which the energy in the energy storage means or capacitor arrangement can be dissipated.

Various other modifications and alterations may be made in the above-described apparatuses in accordance with the present invention, without thereby departing from the spirit and scope of the invention.

I claim:

1. An electrical circuit for generating energy pulses at shock electrodes of a defibrillator, comprising an energy storage means comprising a plurality of capacitors for storing electrical energy, an operating switch between said capacitors and said shock electrodes, said operating switch being closable to discharge the stored energy from the storage means to the shock electrodes in the shock treatment of a patient, a shunt contact means which is connected in parallel with the energy storage means and to a junction on the output side of the operating switch and which is normally closed condition shunts the shock electrodes, means for opening said shunt contact means only for the duration of ths shock treatment, and inductance means, a generator as a power source for said inductance means, said inductance means being connected in series with said shunt contact means, whereby a monitoring voltage signal is produced at said shunt contact means responsive to a high-frequency voltage drop generated at said inductance means, which occurs only when said shunt contact means is closed, and a monitoring means for said monitoring voltage signal.

2. A circuit as set forth in claim 1 including a first voltage barrier means connected between a first terminal of the shunt contact means and a respective said shock electrode and a second voltage barrier means connected between a second terminal of the shunt contact means and another respective said shock electrode.

3. A circuit as set forth in claim 1 further including means for connecting an EKG-apparatus to said electrodes.

4. A circuit as set forth in claim 1 including means for tapping off a monitoring voltage at the shunt contact means, and means for setting a predetermined reference value for said monitoring voltage whereby the shock procedure may be initiated only when said monitoring voltage exceeds said predetermined reference value.

5. A circuit as set forth in claim 1 including means for first opening the shunt contact means and then supplying a signal for discharge of the stored energy from the energy storage means, for said shock treatment.

6. A circuit as set forth in claim 1 and further comprising means for producing a measurement value in respect of the energy storage means, and a receiving circuit means for receiving said measurement value and said monitoring voltage signal and operable to produce signals for closing said operating switch and opening said shunt contact means respectively, in response to given values in respect of said measurement value and said monitoring voltage signal.

7. A circuit as set forth in claim 6 wherein said inductor connected in series with said shunt contact means comprises means for producing a voltage drop for generating an operating voltage for said receiving circuit means, thereby to govern operation thereof in dependence on said voltage drop generating said operating voltage.

8. A circuit as set forth in claim 1 and further including a shock pulse-generating inductance means connected between the operating switch and said junction at which the shunt contact means is connected.

9. A circuit as set forth in claim 1 wherein said energy storage means comprises as plurality of series-connected capacitors chargeable to the same voltage level, and including a plurality of switch means operable for successively discharging said capacitors at given intervals of time.

10. A circuit as set forth in claim 1 wherein said energy storage means comprises a plurality of parallel-connected capacitors chargeable to the same voltage level, and including a plurality of switch means operable for successively discharging said capacitors at given intervals of time.

11. A circuit as set forth in claim 1 and further including first and second shock electrodes, each said shock electrode comprising: a handle portion; an applicator electrode portion adapted to be applied to a person to be treated; means for supplying said electrode portion with energy from said energy storage means; and a protection electrode disposed between said electrode portion and said handle portion and means to electrically conductively connect the protective electrode of said first shock electrode to the protective electrode of said second shock electrode.

12. A circuit as set forth in claim 11 wherein said protection electrode is of an annular configuration.

13. A circuit as set forth in claim 11 wherein said protection electrode is of a disc-like configuration.

14. A circuit as set forth in claim 11 including control switches in said connection means wherein said protection electrodes of said first and second electrodes are connected together.

15. A circuit as set forth in claim 1 and further including a series circuit comprising a discharging switch and a discharging resistor, said series circuit being connected in parallel with said energy storage means, to a junction on the input side of said operating switch.

16. A circuit as set forth in claim 15 wherein said discharging switch comprises a plurality of series-connected thyristors and further comprising means for generating a firing signal having a steep voltage change characteristic for firing said thyristors.

17. A circuit as set forth in claim 16 wherein said operating switch also comprises a plurality of series-connected thyristors adapted to fired simultaneously by a control signal having a steep voltage change characteristic.

18. A circuit as set forth in claim 16 wherein said plurality of capacitors are series-connected with each other and further including a plurality of series-connected Zener diodes, respective pairs of said Zener diodes being connected in parallel with respective ones of said plurality of capacitors, and a plurality of resistor means, each resistor means being connected between at least one of a junction between a said pair of Zener diodes and a junction between adjacent ones of said plurality of capacitors for potential distribution to the thyristors of said discharging switch.

19. A circuit as set forth in claim 16 and further including a plurality of capacitance means each connected between the anode and the control electrode of a said thyristor.

20. A circuit as set forth in claim 1 wherein said operating switch comprises series-connected thyristors adapted to be fired simultaneously by a control signal having a steep voltage change characteristic.

21. A circuit as set forth in claim 20 and futher including series-connected Zener diodes a resistor means to said capacitors for potential distribution to the thyristors of said operating switch.

22. A circuit as set forth in claim 20 and further including respective capacitance means connected between the anode and the control electrode of each said thyristor.

23. An electrode for a defibrillator, comprising: a grip portion of manipulation of said electrode; an applicator electrode portion adapted to be applied to a patient for defibrillation treatment; supply means for supplying electrical pulse energy to said electrode portion from said defibrillator; a protective electrode means disposed between said grip portion and said electrode portion, said protective electrode means comprising an electrode having an aperture through which passes a portion of said supply means for said electrode portion, said protective electrode means not being electrically connected to said supply means; and means to electrically conductively connect said protective electrode means to a protective electrode means of a respective other defibrillator electrode.

24. A shock electrode as defined in claim 23 characterized in that said application electrode portion is shaped like a paddle or spoon for direct placing against a heart muscle.

* * * * *